United States Patent
Russi

(10) Patent No.: US 9,545,260 B2
(45) Date of Patent: Jan. 17, 2017

(54) MINIMALLY INVASIVE DEVICE FOR SURGICAL OPERATIONS

(71) Applicant: Martin Russi, Montevideo (UY)

(72) Inventor: Martin Russi, Montevideo (UY)

( * ) Notice: Subject to any disclaimer, the term of this patent is extended or adjusted under 35 U.S.C. 154(b) by 360 days.

(21) Appl. No.: 14/367,766

(22) PCT Filed: Dec. 21, 2012

(86) PCT No.: PCT/IB2012/057579
§ 371 (c)(1),
(2) Date: Jun. 20, 2014

(87) PCT Pub. No.: WO2013/093865
PCT Pub. Date: Jun. 27, 2013

(65) Prior Publication Data
US 2014/0378977 A1 Dec. 25, 2014

(30) Foreign Application Priority Data
Dec. 22, 2011 (UY) .......................................... 33.839

(51) Int. Cl.
*A61B 17/15* (2006.01)
*A61B 17/04* (2006.01)
(Continued)

(52) U.S. Cl.
CPC ........... *A61B 17/151* (2013.01); *A61B 17/148* (2013.01); *A61B 17/82* (2013.01); *A61B 17/8861* (2013.01);
(Continued)

(58) Field of Classification Search
CPC ..................... A61B 17/0469; A61B 2017/145; A61B 17/148; A61B 17/151; A61B 17/82; A61B 17/8861
See application file for complete search history.

(56) References Cited

U.S. PATENT DOCUMENTS 4,312,337 A * 1/1982 Donohue ........... A61B 17/1796
606/103
4,935,027 A * 6/1990 Yoon ................... A61B 17/0469
606/146

(Continued)

FOREIGN PATENT DOCUMENTS

WO 2010129846 A1 11/2010

OTHER PUBLICATIONS

International Preliminary Report on Patentability for International Patent Application No. PCT/IB2012/057579 mailed Jul. 3, 2014, 12 pages.

(Continued)

*Primary Examiner* — Larry E Waggle, Jr.
(74) *Attorney, Agent, or Firm* — Withrow + Terranova, P.L.L.C.; Vincent K. Gustafon

(57) ABSTRACT

The present invention is related to a minimally invasive device for surgical procedures which generally comprises at least a pair of assembly elements formed by a primary main body and a secondary main body joined together at their proximal and distal ends; a fastening element which is inserted in the distal end of both primary and secondary main bodies respectively, which is employed to keep them joined together; a threading element which is inserted in its inner section from the intermediate section of said device, continues to its proximal end and returns to its intermediate section on the opposite end; and a multifunction element located on the inside of the threading element.

20 Claims, 10 Drawing Sheets

(51) Int. Cl.
*A61B 17/82* (2006.01)
*A61B 17/14* (2006.01)
*A61B 17/88* (2006.01)

(52) U.S. Cl.
CPC ...... *A61B 17/0469* (2013.01); *A61B 2017/145* (2013.01)

(56) References Cited

U.S. PATENT DOCUMENTS

| | | | | |
|---|---|---|---|---|
| 6,086,596 | A * | 7/2000 | Durham | A61B 17/8861 606/103 |
| 6,423,080 | B1 | 7/2002 | Gellman et al. | |
| 8,048,080 | B2 | 11/2011 | Bleich et al. | |
| 8,062,300 | B2 | 11/2011 | Schmitz et al. | |
| 2006/0293691 | A1 * | 12/2006 | Mitra | A61B 17/8861 606/103 |
| 2007/0043377 | A1 | 2/2007 | Fernandez | |
| 2010/0286782 | A1 * | 11/2010 | Schaller | A61B 17/14 623/17.12 |

OTHER PUBLICATIONS

International Search Report for International Patent Application No. PCT/IB2012/057579 mailed Jun. 24, 2013, 6 pages.

\* cited by examiner

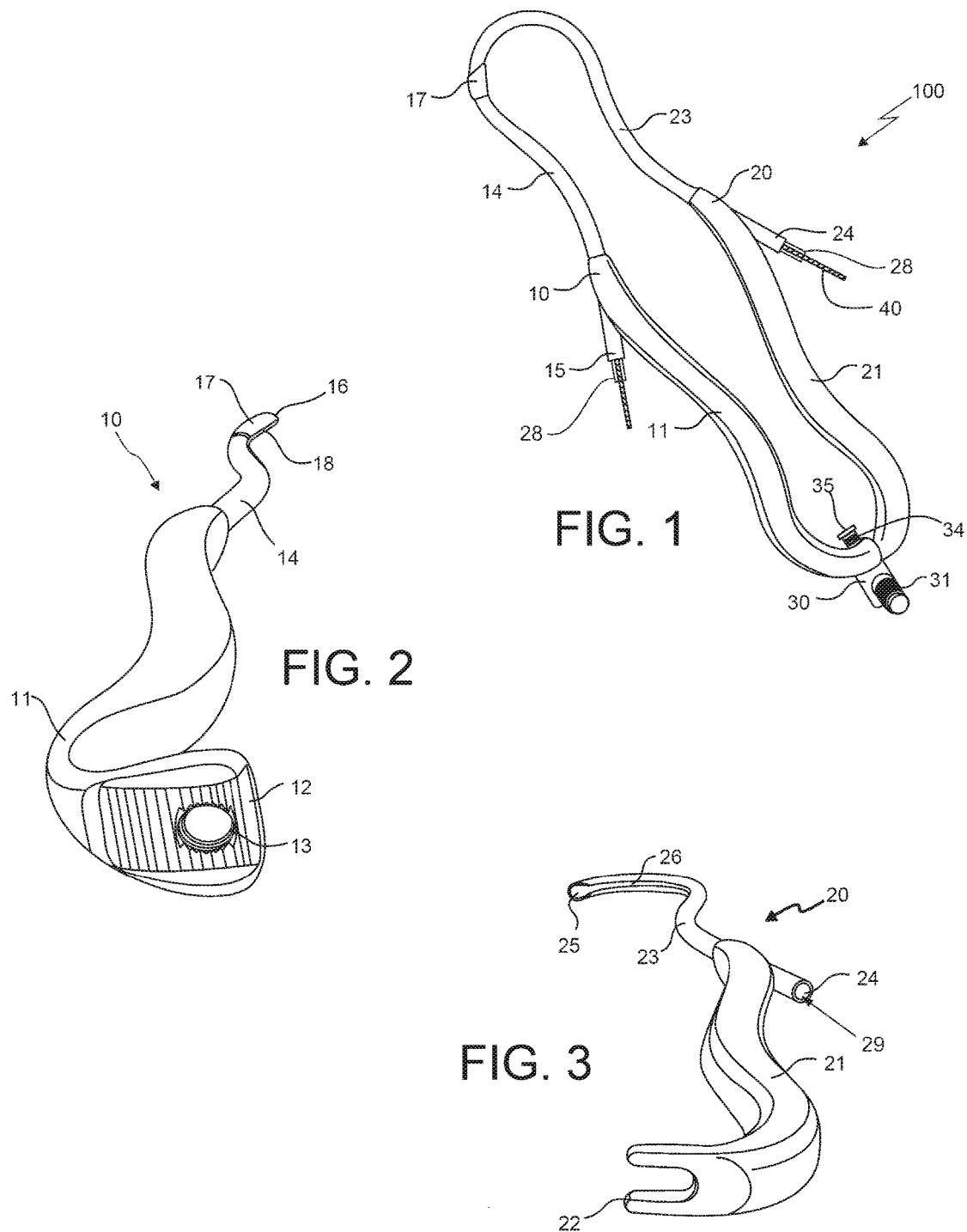

MINIMALLY INVASIVE DEVICE FOR SURGICAL OPERATIONS

STATEMENT OF RELATED APPLICATIONS

This application is a 35 U.S.C. §371 national phase filing of International Application No. PCT/IB2012/057579 filed on Dec. 21, 2012, and further claims priority to Uruguayan Patent Application No. 33.839 filed on Dec. 22, 2011, with the disclosures of the foregoing applications hereby being incorporated by reference herein in their respective entireties.

FIELD OF THE INVENTION

The present invention relates to the field of design and construction of devices used in surgical procedures, such as osteotomies, and specifically relates to a minimally invasive device for surgical procedures.

BACKGROUND OF THE INVENTION

Nowadays, when a person requires a surgical procedure in the course of which the cutting of a bone structure or removal of tissue adjacent to said bone structure is necessary, the surgeon usually carries out a broad approach both to provide a good view of the operating field as well as to protect the adjacent structures. To achieve this, he must carry out considerably large incisions in the skin, muscles, and other tissue of the patient, placing separators and protection material such as gauze and dressings, to protect noble structures such as nerves, which could otherwise be damaged in the course of the cutting procedures. In addition to the risk of damaging organs or surrounding tissue in the area where the incisions are carried out, there is also the risk of cutting a blood vessel which could render the surgical procedure more difficult and dangerous.

In the prior art there are several devices to carry out cuts in bone structures and/or the removal of tissue, which use protecting elements to avoid damage to contiguous structures or organs. Such is the case of the device described in U.S. Pat. No. 8,062,300 B2, which is formed by an elongated main body which comprises a proximal handle, a distal handle, a guiding conduit and a guiding wire; these latter two elements connecting the proximal and distal handles. The proximal handle is connected to a guiding conduit, which is formed by a rigid proximal section and a flexible distal section, at the end of which a coupling element is located, which enables connection between said guiding conduit and a guiding wire. On one of the surfaces of the flexible distal section, tissue modifying elements are located, which carry out the material removal function of said device.

To keep the tissue modifying elements from damaging structures or tissues before they have reached the working area, they are covered by a protective cover, made preferably from polymer material. The guiding wire is coupled on its other end to the distal handle, which includes a tensioning element which is used to modify the tension level of the guiding wire.

However, the above device described above has a drawback in that its design is not ergonomic, which makes its use by the medical team more difficult. Another disadvantage is that the cut carried out by the device is performed by material removal instead of a clean cut, as well as the further drawback that being a very flexible device, only very small structures may be cut. In addition to the above, said device does not include a mechanism which enables regulation and measurement of the cut in the spatial planes.

Another example of devices found in the prior art is the one described in U.S. Pat. No. 8,048,080 B2, which comprises a main body formed by an elongated body, a handle, an actuator, tissue modifying elements and a protecting surface. The elongated body has a proximal and a distal section, which includes a window to enable the tissue modifying elements to make contact with the tissue to be modified. Before introducing the elongated body in the area with tissues to be modified, a guide piece must be inserted, which will act as guide and support element for said main body; as the elongated body is introduced in the body of the patient, the guide piece is inserted in the central part of said elongated body, once the elongated body is placed in its working position, the free end of the guide piece which projects outwards from the body of the patient is held firmly; the handle is held firmly as well, and by operating the actuator, the tissue modifying elements begin to carry out their abrasion or cutting function. Once the procedure is completed, the main body and the guide piece are removed from the body of the patient.

The above described device, because of its configuration and design, requires at least two people to perform adequately, since it is required that the opposite end of the guide piece is firmly held, either by means of an anchoring device or by the hand of an operator. As in the case of the device of U.S. Pat. No. 8,062,300 B2, said device cuts by abrasion and not by means of a clean cut, and does not include a mechanism which allows regulation and measurement of the cut on any spatial plane.

A further example of devices in the prior art can be found in U.S. Pat. No. 6,423,080 B1 which describes a device employed to hold or secure structures and/or organs, which comprises a pair of positioning pieces, which are formed by a handle, a guiding conduit, a bracket, a cutting element and an actuator. The handle has a hollow tubular body which has an actuator in its upper section and a bracket in its lower section which holds the guiding conduit in position. Said handle has an irregular outer surface to improve the grip.

The guiding conduit has a straight proximal section, a curved intermediate section and a straight distal section. In an additional embodiment of said device, the straight distal section is oriented at a 90° angle with respect to the position of the straight proximal section. In addition, the guiding conduit is hollow to house the cutting element which in turn is hollow to allow passage of the guiding piece. The cutting element is employed to create a small aperture in the tissue and allow passage of the positioning element.

One of the main disadvantages of said device is that it is conceived solely to locate a cord or sling on a tissue or structure that so requires, not for cutting bone structures. In addition to the above, to position the cord or sling requires removal of both positioning elements and of the guiding piece, which makes operating the device considerably difficult.

BRIEF DESCRIPTION OF THE INVENTION

In order to overcome the disadvantages of the prior art, a minimally invasive device for carrying out surgical procedures has been developed, which generally comprises at least a pair assembly elements formed by a primary main body and a secondary main body, joined at their proximal and distal ends; a fastening element which is inserted in the distal end of both primary and secondary main bodies respectively, whose function is to hold them together; a threading element which is inserted in its inner section from the intermediate section of said device, continues to its proximal end and returns to the intermediate section by the opposite end; and a multifunction element which is located inside the threading element.

The primary main body is formed by a primary holding handle and a primary positioning element which connects with the primary holding handle. In the most distal part of the primary holding handle, an anchoring area is located, which includes a threaded hole where the fastening element is screwed. In addition, the primary positioning element has a first slit oriented towards the inner part of the primary main body, which, together with a second slit located in the secondary main body is used so that the multifunction element may protrude and carry out its work.

The secondary main body is formed by a secondary holding handle and a secondary positioning element which connects with the primary holding handle. At the most distal section of the secondary holding handle, a coupling element is located, with a shape resembling a horizontal "U". In addition, the secondary positioning element has a second slit oriented towards the inner part of the secondary main body, which enables that, together with the first slit of the primary positioning element, the multifunction element may protrude on the inside of the present device for surgical procedures. The fastening element is formed by a central handhold with an outside surface having a plurality of channels to increase the grip of said handhold. On its lower end, a boss is located, from which a threaded pin of smaller diameter projects, which is inserted in the threaded hole in the anchoring area of the primary main body.

Once the primary positioning element is joined to the secondary positioning element at the proximal end, an internal channel is formed at the ends of which the threading element is placed. Said threading element houses the multifunction element in its interior. The internal channel has a window which is formed by joining the first slit to the second slit which enables the multifunction element to protrude from the inner part of the device.

The multifunction element is employed to perform several tasks, among others: to modify tissues and/or structures, suturing, loops and cuts in bone structures.

When this device is employed to cut bone structures, it includes a spatial positioning element which enables it to direct, measure and graduate the cut in said bone structure on three spatial planes, frontal sagittal and rotational. Said element is formed by a straight arm, where a first central longitudinal channel is located which runs along its entire length, a curved arm where a second longitudinal channel is located, and an anchoring mechanism employed to attach the spatial positioning element to the surgical procedures device.

In an additional embodiment of the present device, it consists of a single body, which has a holding handle which projects from its distal end to approximately two third parts of the total length of said device, and a cutting body which projects from the end of the holding handle to the proximal end of said device.

It is important to point out that the structure of the device for surgical procedures subject of the present invention allows its use in long bone osteotomies, mainly femur and shinbone, for procedures such as bone lengthening, axial corrections of members, as well as osteotomies of flat bones such as the illiacus, ischium and pubis.

BRIEF SUMMARY OF THE INVENTION

Bearing in mind the shortcomings of the prior art, one of the objects of the present invention is to provide a device for use in surgical procedures which requires minimal invasion, and which may be used in osteotomy and/or tissue removal procedures in a convenient and simple way An additional object of the present invention is to provide a device for use in surgical procedures which requires minimal invasion and which reduces to a minimum the time required to carry out the surgical procedure and the internal damage caused to the patient.

An additional object of the present invention is to provide a minimally invasive device for use in surgical procedures which enables carrying out surgical procedures which are safer and less invasive for the patient.

A further object of the present invention is to provide a minimally invasive device for surgical procedures with ergonomic design and construction, thereby facilitating its handling by the medical team.

An additional object of the present invention is to provide a minimally invasive device for surgical procedures which includes a threading element which enables threading and placement of a multifunction element, such as for example a Gigli saw, to allow cutting of a bone structure.

Another of the objects of the present invention is to provide a minimally invasive device for surgical procedures which functions as a protective element to avoid damage to adjacent structures and/or tissues during threading and use of the multifunction element.

Another of the objects of the present invention is to provide a minimally invasive device for surgical procedures which includes means to attach it to a bone structure and a spatial positioning element which enables adjustment of the cut of said bone structure in the three planes, sagittal, frontal and rotational.

BRIEF DESCRIPTION OF THE DRAWINGS

The novelty aspects which are considered to characterize the present invention will be specifically established in the attached claims. However, the invention itself, as well as its structure and operation, along with other functions and advantages, will be better understood in the following detailed description of a preferred embodiment, when it is read in relation to the attached drawings, in which:

FIG. 1 is a front perspective view of a preferred embodiment of the minimally invasive device for surgical procedures subject of the present invention.

FIG. 2 is a lower perspective view of the primary main body which forms part of the device for surgical procedures shown in FIG. 1.

FIG. 3 is a lower perspective view of the secondary main body which forms part of the device for surgical procedures shown in FIG. 1.

DETAILED DESCRIPTION OF THE INVENTION

Figure 4:
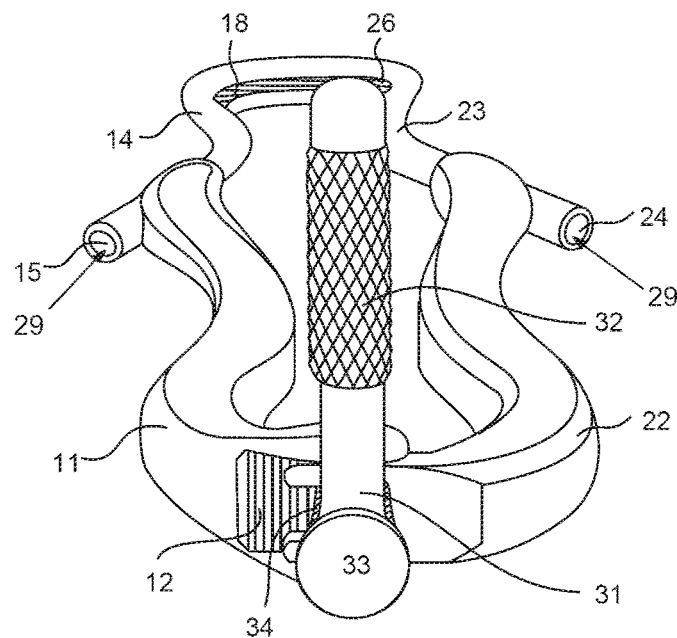
FIG. 4 is a lower perspective view of the device for surgical procedures shown in FIG. 1.
Figure 5:
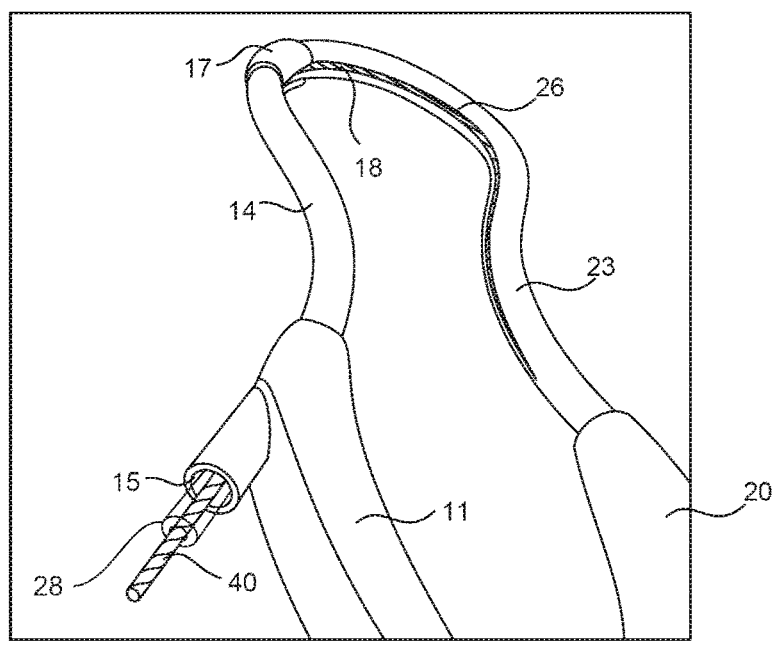
FIG. 5 is a partial lower and front perspective view of the device for surgical procedures shown in FIG. 1.

Referencing the attached drawings, and more specifically FIGS. 1 to 5 of said drawings, they show a minimally invasive device 100 for surgical procedures constructed according to a particularly preferred embodiment of the present invention, which should be considered as representative but not limitative of the same, where said device 100 comprises in general terms at least a pair of assembly elements formed by a primary main body, 10 and a secondary main body 20 joined at their proximal and distal ends; a fastening element 30 which is inserted in the distal end of both the primary and secondary main bodies 10 and 20 respectively, which is used to keep them joined together; a threading element 28 (shown in FIGS. 1 and 5) which is inserted in its inner section from the intermediate section of device 100, continues to its proximal end and returns to the intermediate section by the opposite end, and a multifunction element 40 which is located inside the threading element 28.

For better understanding of the structural configuration of the device for surgical procedures 100, it is important to define that said device 100 has a proximal end, which is the end located closest to the tissue or bone structure to be modified or cut, an intermediate section, which is located approximately in the central part of device 100, and a distal end, which corresponds to the opposite end with respect to the proximal end, that is to say, corresponds to the end furthest from the tissue or structure to be modified.

The primary main body 10 which corresponds to an assembly element of the above mentioned device 100, which in FIG. 1 is located on the left side of said device 100, is formed by a primary holding handle 11 which projects from the base of the distal end of device 100 to the intermediate section of said primary main body 10; and a primary positioning element 14 which connects to the primary holding handle 11, and projects from the intermediate section of the primary main body 10 to its proximal end.

The primary main holding handle 11 is a solid body that together with a secondary holding handle 21, form the shape of a fork, at whose distal section an anchoring area 12 is located, which has a homogeneous serrated surface on its outer face, whose function will be described below. In addition, said anchoring area 12 of the primary holding handle 11 has a threaded orifice in which fastening element 30 is threadingly inserted.

The primary positioning element 14 is formed by a cylindrical hollow body which together with a secondary positioning element 23 resemble the shape of the upper part of a bowling pin, whose bottom end 15 projects laterally from the intermediate section of primary main body 10 towards the outer part of device 100 such as can be seen in FIG. 1. At its upper end 16, primary positioning element 14 has a coupling body 17, preferably of annular shape and with an inside diameter equal to the outside diameter of the body of primary positioning element 14. In addition, said primary positioning element 14 has a first slit 18 oriented towards the inner part of primary main body 10, which in a preferred embodiment, runs longitudinally from its upper end 16 to approximately half of the total length of said primary positioning element 14. In another embodiment, slit 18 is complete since it runs longitudinally along the entire inner length of primary positioning element 14. First slit 18 together with a second slit 26 located in secondary main body 20, is used so that multifunction element 40 may protrude and carry out its work. The complete slit allows multifunction element 40 to act in its entire length, enabling suturing, cerclage, etc. without the need to remove device 100.

The other assembly element of device 100 corresponds to secondary main body 20, which is located in FIG. 1 on the right hand side of said device 100, being formed by a secondary holding handle 21 which projects from the base of the distal end of said secondary main body 20 to the intermediate section of the secondary main body 20; and a secondary positioning element 23 which projects from the end of the secondary holding handle 21, that is to say, from the intermediate section of said secondary main body 20 to the base of its proximal end.

Secondary holding handle 21 is a solid body that together with primary holding handle 11, resemble the shape of a fork, at the most distal section of which a coupling element 22 is located, which has the shape of a horizontal "U", such as may be seen in FIG. 3. On its inside face, said coupling element 22 has a homogeneous serrated surface (not shown in the figures) which corresponds in shape and size to the homogeneous serrated surface of anchoring area 12 of primary holding handle 10.

Secondary positioning element 23 is formed by a hollow cylindrical body, which together with primary positioning element 14 resemble the shape of the upper part of a bowling pin, whose lower end 24 projects from the intermediate section of secondary main body 20 to the outer part of device 100. The upper end 25 of said secondary positioning element 23 has a diameter which enables it to be inserted in the coupling body 17 located in primary positioning element 14. In addition, said secondary positioning element 23 has a second slit 26 oriented towards the inner part of secondary main body 20, which in a preferred embodiment runs longitudinally from its upper end 25 to approximately half of the total length of said secondary positioning element 23. In an additional embodiment, slit 26 is complete since it runs longitudinally along the entire inner section of secondary positioning element 23. Second slit 26 is used so that, together with first slit 18 of primary positioning element 14, they allow multifunction element 40 to protrude on the inside of device 100.

Primary main body 10 is joined to secondary main body 20 at their proximal and distal ends, forming a single circuit body, with a shape which resembles an inverted fork in its distal part and the outline of a bowling pin in its proximal part. It is worth mentioning that at the proximal end of the device for surgical procedures 100, primary positioning element 14 is joined to secondary positioning element 23 by means of coupling body 17 of primary positioning element 14. The function of holding together primary main body 10 and secondary main body 20 at their distal end is carried out by fastening element 30.

Fastening element 30 is formed by a central handle 31 of preferably cylindrical shape, with an outside surface having a plurality of channels 32 which cross each other to form a rough surface which increases grip of said central handle 31. At the lower end of central handle 31 is located a boss 33 positioned perpendicularly to said central handle 31, with a preferably cylindrical outline, from the inside of which a threaded cylinder 34 of smaller diameter than said boss 31 projects, which is placed in threaded orifice 13 of anchoring area 12 of primary main body 10. Threaded cylinder 34 has a diameter which enables it to be firmly held by coupling element 22. In addition, at the opposite end of where boss 33 is located, threaded cylinder 34 has a protrusion 35, which is an integral part of threaded cylinder 34 and of larger diameter than threaded hole 13 of anchoring area 12, which once fastening element 30 is placed in primary main body 10 ensures that it cannot be separated from said body 10 but may rotate freely to fasten secondary main body 20.

Once primary positioning element 14 is joined to secondary positioning element 23 at its proximal end, and because both elements are formed by hollow cylindrical bodies, an internal channel is formed at the ends of which a threading element 28 is placed (shown in FIGS. 1 and 5), which is inserted from the intermediate section of device 100, continues to its proximal end, and returns to the intermediate section on the opposite side. The internal channel has an aperture (window) which is formed by joining first slit 18 of primary positioning element 14 to second slit 26 of secondary positioning element 23 and from where multifunction element 40 may protrude on the inner part of device 100 as will be explained below.

Multifunction element 40 is employed to perform several functions, including but not limited to: modifications in tissues and/or structures, sutures, cerclages, loops and cuts in bone structures. Depending on the function to be carried out, multifunction element 40 may be selected from wires, cables, suturing threads and cutting saws, such as for example Gigli's saw, etc.

Over multifunction element 40 a threading element 28 is placed (shown in FIGS. 1 and 5) which in a preferred embodiment of the present invention is a siliconed tube, which facilitates threading of the multifunction element through the internal channel, preventing said element 40 from protruding from the aperture (window) formed by first slit 18 and second slit 26. In addition, if multifunction element 40 has sharp edges as in the case of cutting saws, the threading element 28 protects the person manipulating multifunction element 40 from suffering lesions when placing it in position.

Figure 6:
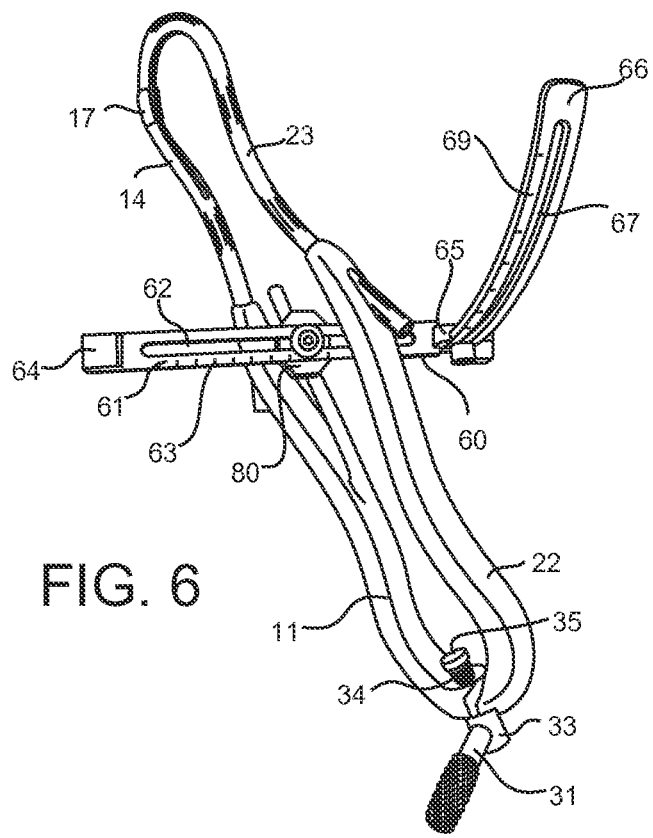
FIG. 6 is a side perspective view of the device for surgical procedures shown in FIG. 1 when connected to a spatial positioning element.
Figure 7:
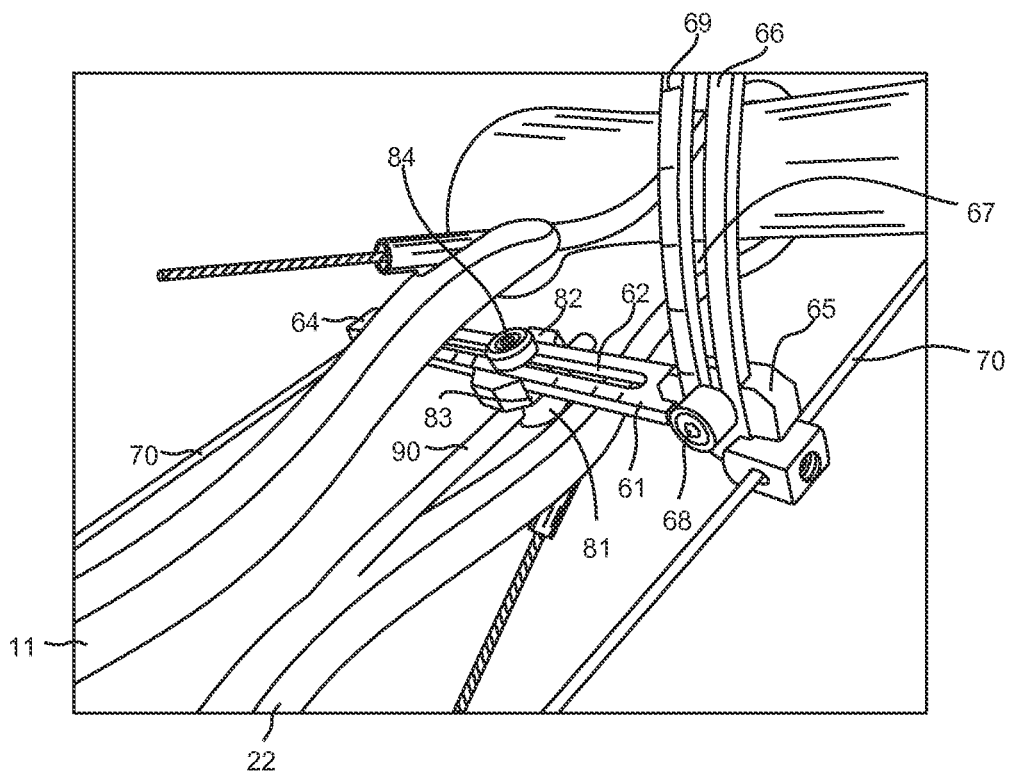
FIG. 7 is a partial side perspective view of the arrangement shown in FIG. 6, which is attached to a bone structure.

As is shown in FIGS. 6 and 7, device 100 may be used for cutting bone structures, and for this purpose said device 100 includes an element for spatial positioning 60 which enables it to direct, measure and graduate the cut of said bone structure on three spatial planes: frontal sagittal and rotational. To use spatial positioning element 60 it is firmly attached to the bone structure to be cut by at least two external anchoring elements 70 and to the device for surgical procedures 100 by means of an anchoring mechanism 80. This positioning and graduation device allows us to maintain the bone structure in position after the cut even after removing device 100.

Spatial positioning 60 is formed by a straight arm 61, which has a flat elongated body of rectangular shape, where a first central longitudinal channel 62 is located, which traverses the whole thickness of the body and runs along its entire length and over which anchoring mechanism 80, which is described below, slides and to which it is secured. Said straight arm 61 has a first indicating scale 63 on its upper surface, which allows the user of this device to read the displacement of device 100 on the frontal plane (varus-valgus).

Straight arm 61 has a primary anchoring point 64 on one of its ends, preferably of quadrangular shape, which is provided with a central orifice (not shown in the figures) where an external fastening element 70 is inserted. At the opposite end with respect to the location of primary anchoring point 64, a sliding anchoring point 65 is located, which in a preferred embodiment is in the shape of a "C" over which a curved arm 66 slides and to which it is secured.

Curved arm 66 is formed by a thin curved body with a curvature having a radius equal to the distance to the center of the bone structure to be cut and where a second central longitudinal channel 67 which traverses the whole thickness of the body is located, which is used to fasten said curved arm 66 to the sliding anchoring point 65 by means of a screw 68 which is threadingly inserted in an orifice (not shown in the figures) located in sliding anchoring point 65. Curved arm 66 includes an indicating scale 69 on its front surface, which enables measurement of the rotation angle of device 100 with respect to the bone structure. This feature is particularly useful in derotational osteotomies.

The pair of external fastening elements 70 is used to attach device 100 to a bone structure. Said pair of external fastening elements 70 is selected from a group including Kirschner and/or Steinmann pins, the preferred element being Kirschner pins.

Anchoring mechanism 80 is employed to secure spatial positioning element 60 to device for surgical procedures 100. To achieve this, primary main body 10 or secondary main body 20 of device 100, and particularly primary holding handle 11 or secondary holding handle 21 include an appendix 90 preferably of cylindrical shape which protrudes longitudinally and upwards following a straight trajectory, from approximately the middle of holding handle 11 or 21 to a distance that coincides with the end of primary holding handle 11 or secondary holding handle 21.

In this preferred embodiment, anchoring mechanism 80 is formed by a main body 81, preferably of cylindrical shape, the front face of which includes an orifice (not shown in the figures) in which appendix 90 of primary holding handle 11 or secondary holding handle 21 is inserted and secured. The depth at which device 100 is located with respect to the bone structure to be cut is graduated depending on the position in which anchoring mechanism 80 is secured to appendix 90 with respect to its longitudinal axis. In addition, on the upper face of said main body 81, a rotation element 82 is located, which can rotate with respect to main body 81 and which includes a preferably rectangular indentation 83. Said indentation 83, has a threaded orifice in its center (not shown in the figures), over which straight arm 61 is positioned and secured by a bolt 84 which is inserted in first central channel 62 and in said threaded orifice. The configuration of main body 81 with respect to rotation element 82 allows rotation of device 100 with respect to the spatial positioning element 60, which enables control of the bone structure cut on the sagittal and frontal planes. Said feature is very useful in varus-valgus osteotomies or when it is necessary to create a fore wedge in a hip or knee extension osteotomy.

Figure 8:
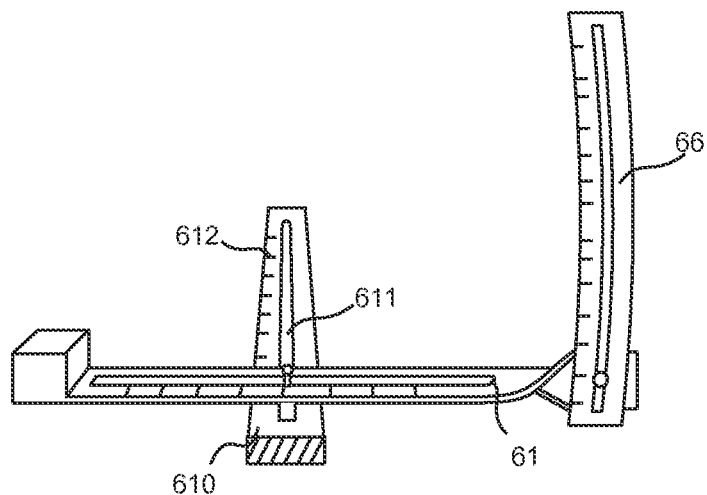
FIG. 8 is a front perspective view of a first embodiment of the spatial positioning element which forms part of the device for surgical procedures.
Figure 9:
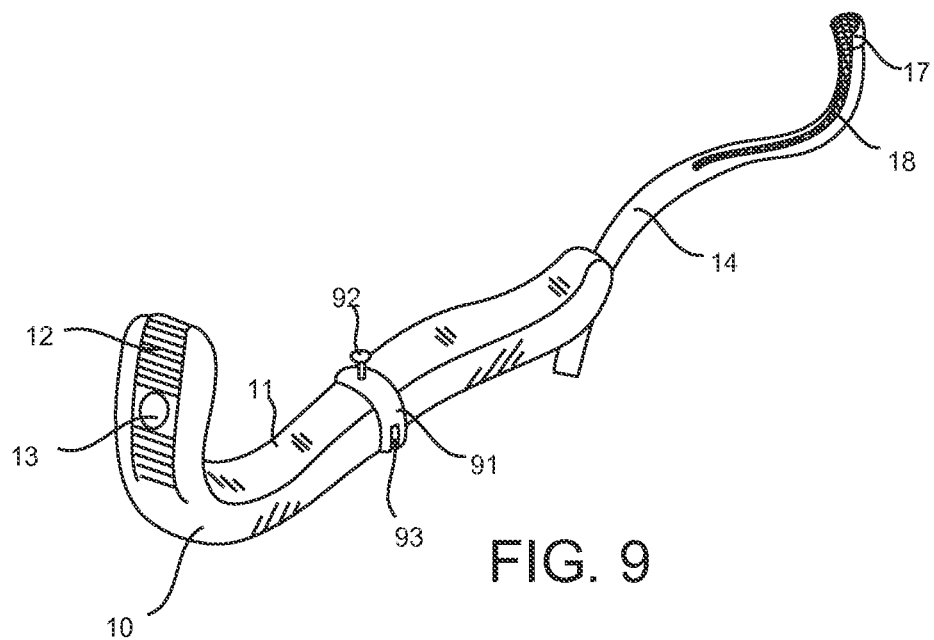
FIG. 9 is a side perspective view of a ring located in the primary main body, which is part of the first embodiment of the spatial positioning element shown in FIG. 8.

In a first additional embodiment of the spatial positioning element 60 shown in FIGS. 8 and 9, said element 60 includes, in addition to straight arm 61 and curved arm 66, an intermediate arm 610 arranged below straight arm 61, which has a flat elongated body of rectangular shape, where a third central channel 611 is located, which traverses the entire thickness of the body and runs along its entire length. It is important to mention that intermediate arm 610 performs the same function as appendix 90, that is, it allows to graduate the depth at which device 100 is located with respect to the bone structure to be cut, and for that purpose, said intermediate arm 610 has a third indicating scale 612 on its outer upper face.

In addition, over left primary main body 10 or over right main body 20 of device 100, more specifically over primary holding handle 11 or over secondary holding handle 21, a ring 91 is located, which is part of a first additional embodiment of anchoring mechanism 80, which includes a fixed coupling element 92 located centrally on its upper outer face, which is employed to connect to spatial positioning element 60 by coupling to intermediate arm 610; a quick locking mechanism (not shown in the figures) to allow fast coupling of said ring 91 to device 100, and an intermediate indentation 93 located on its lower outer surface, which allows movement of device 100 to graduate and control the cut of the bone structure on the sagittal plane.

Figure 10:
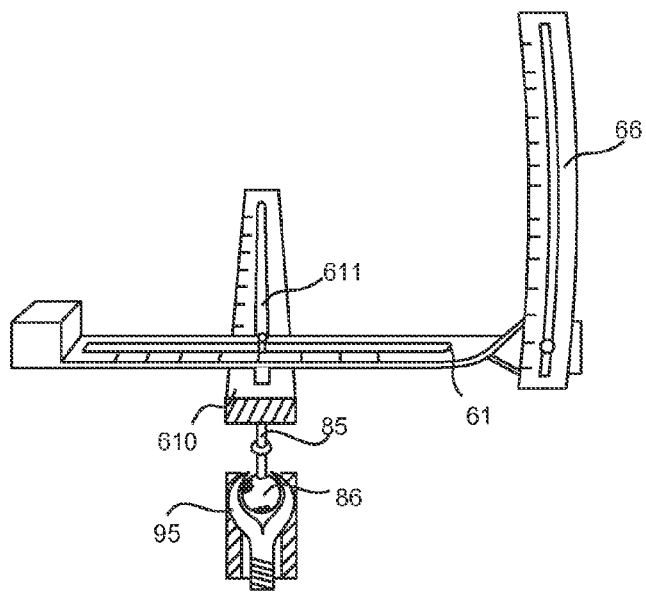
FIG. 10 is a front perspective view of a second embodiment of the spatial positioning element which forms part of the device for surgical procedures.
Figure 11:
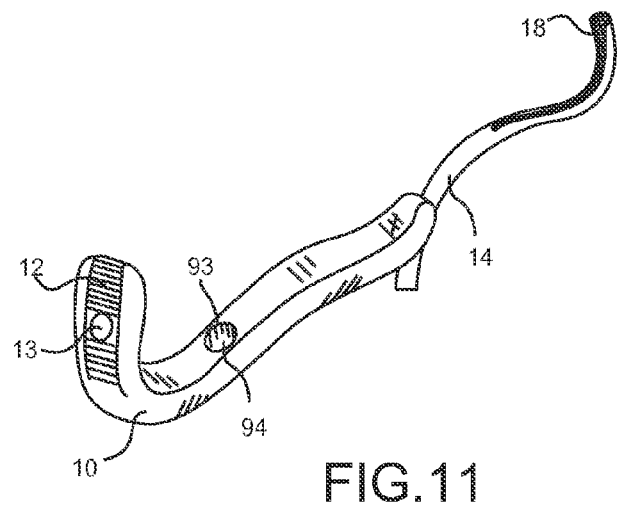
FIG. 11 is a side perspective view of a retaining system located in the primary main body, which forms part of the second embodiment of the spatial positioning element shown in FIG. 10.

Regarding FIGS. 10 and 11, they show a second additional embodiment of spatial positioning element 60, where said element 60, in addition to including a straight arm 61, a curved arm 66 and an intermediate arm 610 as described in the first embodiment of said element 60, includes a vertical stem 85, the lower end of which includes a sphere 86, which, as will be described below, is inserted in a spherical cavity 94 located in device 100, allowing rotational movement of spatial positioning element 60 with respect to said device 100; while the upper end of said vertical stem 85 is inserted in the first central channel 611 of intermediate arm 610, in such a way that both straight arm 61 and intermediate arm 610 are connected by said vertical stem 85.

In order that this second additional embodiment of spatial positioning device 60 may be connected to device 100, primary main body 10 or secondary main body 20, and particularly primary holding handle 11 or secondary holding handle 21 include a second embodiment of anchoring mechanism 80, which includes a retaining indentation 93 in the shape of a wine glass, which has a spherical cavity 94 on its upper end to retain sphere 86 of vertical stem 85 in such a way as to form a ball joint, and on its lower end, which has a tubular shape and is threaded, said retaining indentation 93 includes a threaded holding key 95 in the shape of a "Y", the vertical end of said "Y" being inserted in the lower end of retaining indentation 93. Threaded key 93, when rotated in one direction, firmly grasps sphere 86, when turned in the opposite direction the force with which sphere 86 is held is diminished, thus allowing angular movement of device 100 over spatial positioning element 60 on the sagittal plane.

It is important to mention that the structure of the device for surgical procedures 100 subject of the present invention allows its use in long bone osteotomies, particularly in the case of femur and shinbone, for procedures such as bone lengthening, axial corrections of members, as well as flat bone osteotomies, as in the case of the illiac, ischion and pubic bones.

Figure 12:
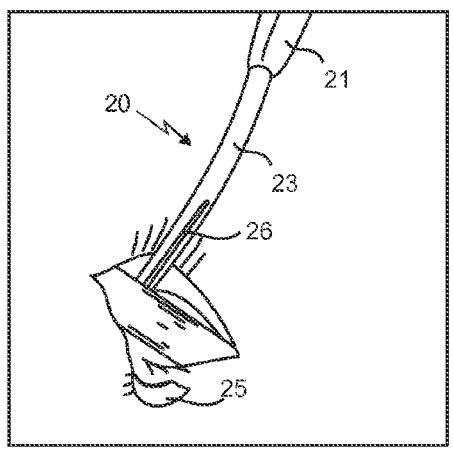
FIG. 12 is a perspective view of the secondary main body being placed around a bone structure to carry out an osteotomy.
Figure 13:
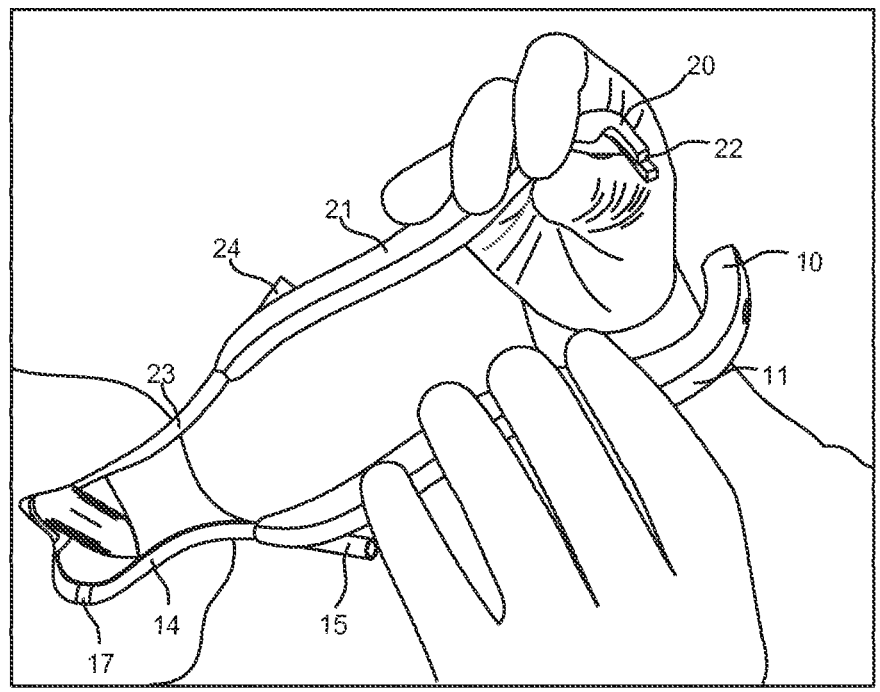
FIG. 13 is a perspective view of the primary main body and the secondary main body being joined prior to an osteotomy.
Figure 14:
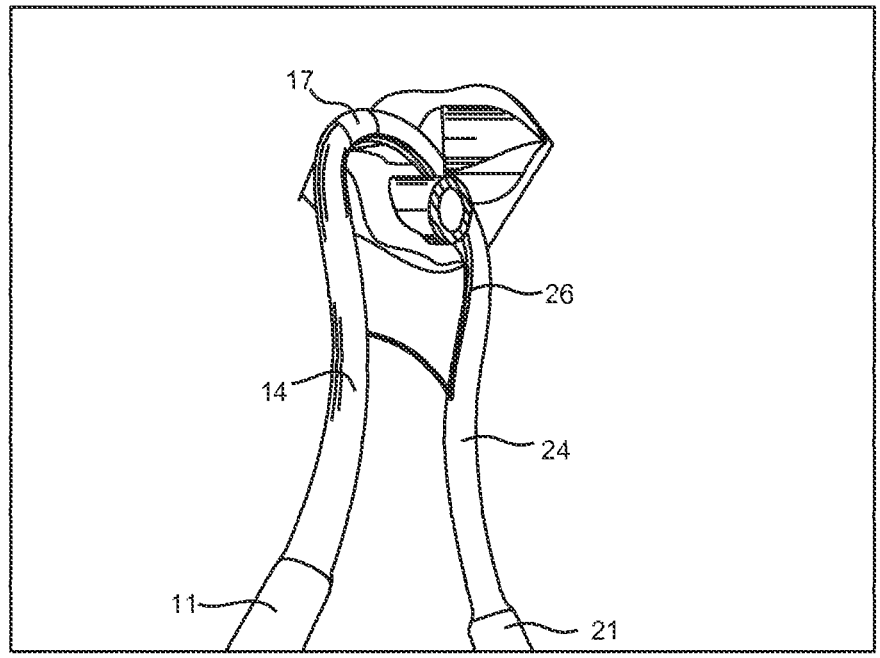
FIG. 14 is a perspective view of a bone structure which has been cut using the device for surgical procedures shown in FIG. 1.

Regarding FIGS. 12 to 14, they show the preferred embodiment of this device 100 being used in a minimally invasive surgical procedure, and specifically being used to perform an osteotomy. Once the surgeon has separated the periosteoum uncovering a bone structure to be cut, the surgeon places the secondary main body 20 of device 100 around said bone structure, in such a way that it is surrounded by secondary positioning element 23, as can be seen in FIG. 12. Once secondary positioning element 23 is located in its working position, it is connected at its proximal end with primary positioning element 14 by means of coupling body 17, as shown in FIG. 13.

In addition, at the distal end of the present device 100, both holding handles 11 and 21, are connected by fastening element 30 (shown in FIGS. 1 to 3). First the serrated internal surface of coupling element 22 of secondary holding handle 21 is placed on the outer surface of anchoring area 12, in such a way that both serrated surfaces mate. Then, threaded projection 34 of fastening element 30 is threaded in orifice 13 of primary holding handle 11 until boss 33 firmly contacts coupling element 22. This allows coupling of both primary and secondary main bodies 10 and 20 respectively in such a way that they cannot become accidentally separated.

Once the present device 100 has been placed in its working position and its proximal and distal ends have been fastened, spatial positioning element 60 is placed on device 100 and attached to the bone structure by a pair of Kirschner nails which constitute fastening elements 70. Once the position and direction of device 100 have been graduated according to the cut to be carried out, the threading element 28 which houses multifunction element 40, which in this case is a Gigli saw, is inserted through lower end 15 of the primary positioning element 14 or through lower end 24 of secondary positioning element 23. Said threading element 28 is inserted in one of the lower ends 15 or 24 and exits on the lower end of the opposite side. When the threading element 28, together with multifunction element 40 are located in their working position, the surgeon removes the threading element 28 uncovering the cutting elements of the Gigli saw. The surgeon grasps both elements of multifunction element 40 protruding from device 100, and by means of a back and forth movement, said element 40 cuts the bone structure through the opening located on the internal channel of the proximal end of device 100.

Figure 15:
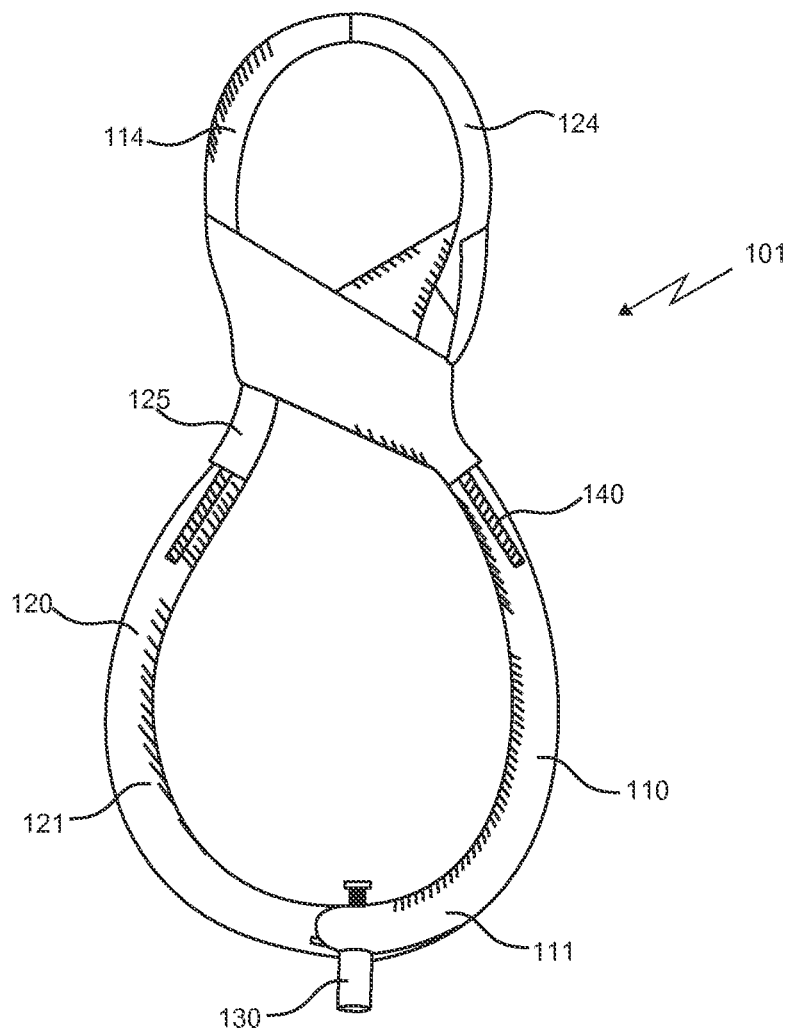
FIG. 15 is a front view of a first additional embodiment of the minimally invasive device for surgical procedures subject of the present invention.
Figure 16:
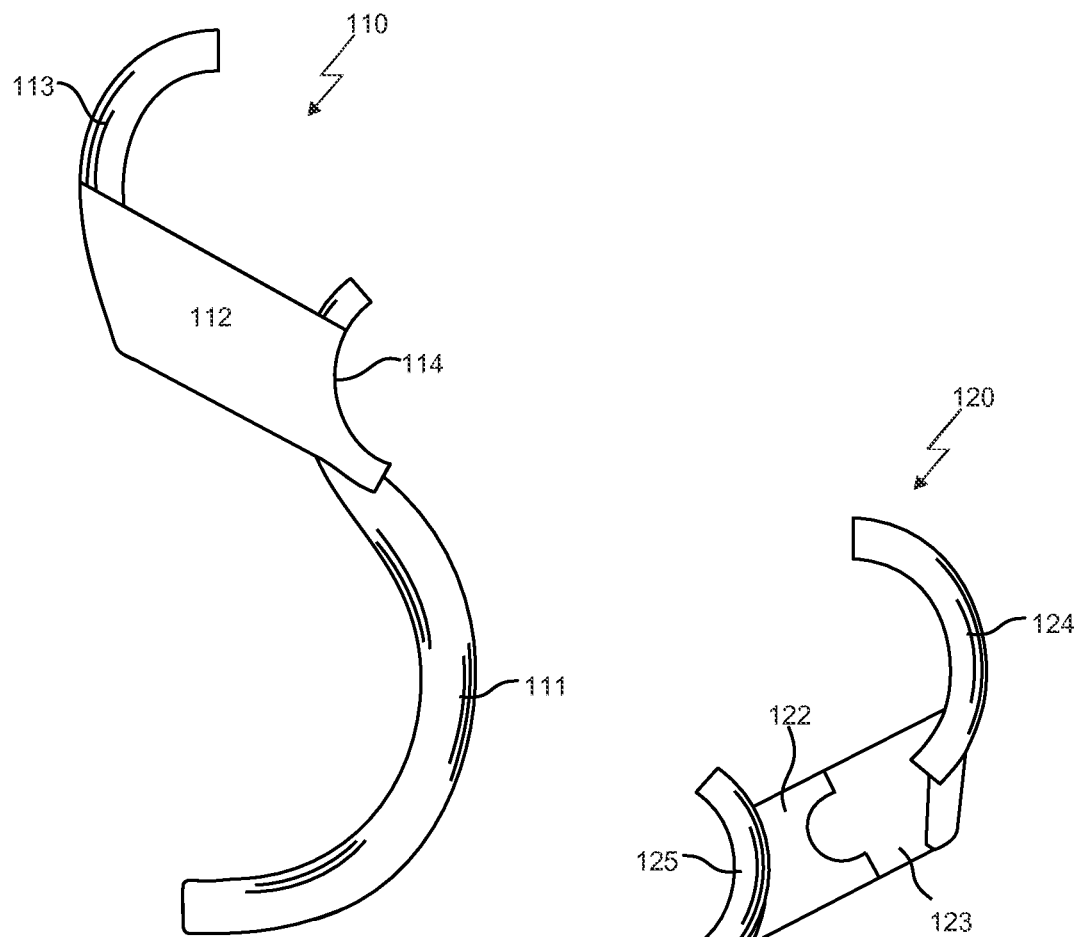
FIG. 16 is a front view of the primary main body which forms part of the device for surgical procedures shown in FIG. 15.
Figure 17:
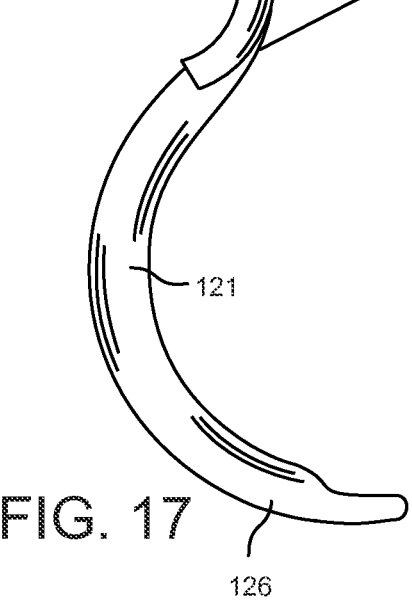
FIG. 17 is a front view of the secondary main body which forms part of the device for surgical procedures shown in FIG. 15.

Regarding FIGS. 15 to 17, they show a first additional embodiment of the minimally invasive device for surgical procedures 101 which is formed by at least a pair of assembly elements formed by a primary main body 110 and a secondary main body 120 joined together crosswise at their proximal and distal ends and at their intermediate section, a fastening element 130 which is inserted in the distal end of both primary and secondary main bodies 110 and 120 respectively, a threading element (such as the threading element 28 shown in FIGS. 1 and 5) which is placed through the internal section of device 101 from its intermediate section, continues to its proximal end and returns to said intermediate section, and a multifunction element 140 which is placed inside the threading element.

As is shown in FIG. 16, the primary main body 110 has the shape of a letter "S" in a front view, and is formed by a primary holding handle 111 of preferably circular transverse section, which forms the lower part of the main body in the shape of a letter "S", projecting from the base of its distal end to approximately the middle section of said primary main body 110, a primary coupling element 112, which constitutes the central part of the main body 110 in the shape of a letter "S", of flat shape, which joins the upper end of primary holding handle 111 to the lower end of a primary positioning element 113, a projection (not shown in the figures) located on the rear face of primary coupling element 112, of preferably cylindrical shape, a primary positioning element 113 which projects from the end of primary coupling element 112 to the proximal end of primary main body 110 thus forming the upper part of the letter "S", and a first complement of positioning element 114 located over the upper end of primary holding handle 111 at the intermediate section of device 101, with a trajectory in the shape of a letter "C" following approximately the outline of primary holding handle 111.

At the most distal part of primary holding handle 111 an anchoring area is located (not shown in the figures) which has a homogeneous serrated surface on its outer face. In addition, on said anchoring area, primary holding handle 111 has a threaded orifice, into which fastening element 130 is threadingly inserted.

Primary positioning element 113 is shaped as a hollow cylindrical body with a first slit (not shown in the figures) oriented towards the inner part of primary main body 110, and which runs along its entire length. In addition, the first complement of positioning element 114 is also shaped as a hollow cylindrical body.

On the other hand, secondary main body 120 has the shape of an 180° inverted letter "S" in a front view, and is formed by a secondary holding handle 121 of preferably circular transverse section, which forms the lower part of the main body in the shape of an inverted letter "S", projecting form the base of its distal end to the intermediate section of said secondary main body 120; a secondary coupling element 122, which constitutes the central section of main body 120 in the shape of an inverted letter "S", and of flat shape, which joins the upper end of secondary holding handle 121 with the lower end of a secondary positioning element 124, a receiving cavity 123 located on the front face of secondary positioning element 122, of a shape which allows insertion and placement in its central part, of the projection of primary coupling element 112, which in the embodiment being described has the shape of a semi circumference, a secondary positioning element 124 which projects from the end of secondary coupling element 122 to the proximal end of secondary main body 120 so as to form the upper part of the inverted letter "S", and a second complement of positioning element 125 located over the upper end of secondary holding handle 121 at a height corresponding to the intermediate section of device 101, which has a trajectory in the shape of a 180° inverted letter "C", approximately following the outline of secondary holding handle 121.

A coupling element 126 shaped as a 180° inverted letter "C" is located at the most distal section of secondary holding handle 121. On its inner face, said element has a homogeneous serrated surface (not shown in the figures) which corresponds in shape and size with the homogeneous serrated surface of the anchoring area of primary holding handle 111.

Secondary positioning element 124 is shaped as a hollow cylindrical body which has a second slit (not shown in the figures), oriented towards the internal part of secondary main body 120, which runs along its entire length. In addition, the second complement of positioning element 125 is shaped as a hollow cylinder as well.

Primary main body 110 is joined to secondary main body 120 at their proximal and distal ends, as well as at its intermediate section, forming a single circuit body in the shape of a number eight, with a smaller diameter at its proximal end than at its distal end. Connection of both main bodies 110 and 120 at their distal end is achieved by using fastening element 130, which has the same configuration and features of fastening element 30 described in the preferred embodiment of device 100.

To join primary main body 110 to secondary main body 120 at their intermediate section, the projection located in primary coupling element 122 is engaged with the receiving cavity 123 of secondary coupling element 122, in such a way that said primary coupling element 112 is overlapped crosswise with secondary coupling element 122.

When joining primary main body 110 to secondary main body 120, primary positioning element 113 is aligned with second complement of positioning element 125 and second positioning element 124 is aligned with first complement of positioning element 114, thus forming an inside channel where the threading element (such as the threading element 28 shown in FIGS. 1 and 5) is placed. Multifunction element 140 is located inside the threading element, both elements performing the same functions and having the same features as the threading and multifunction elements 28, 40 described in the preferred embodiment.

It is worth mentioning that when device for surgical procedures 101 is used to cut bone structures, spatial positioning element 60 described in the preferred embodiment of the present device 100 may be attached to one of its holding handles 111 or 121.

Figure 18:
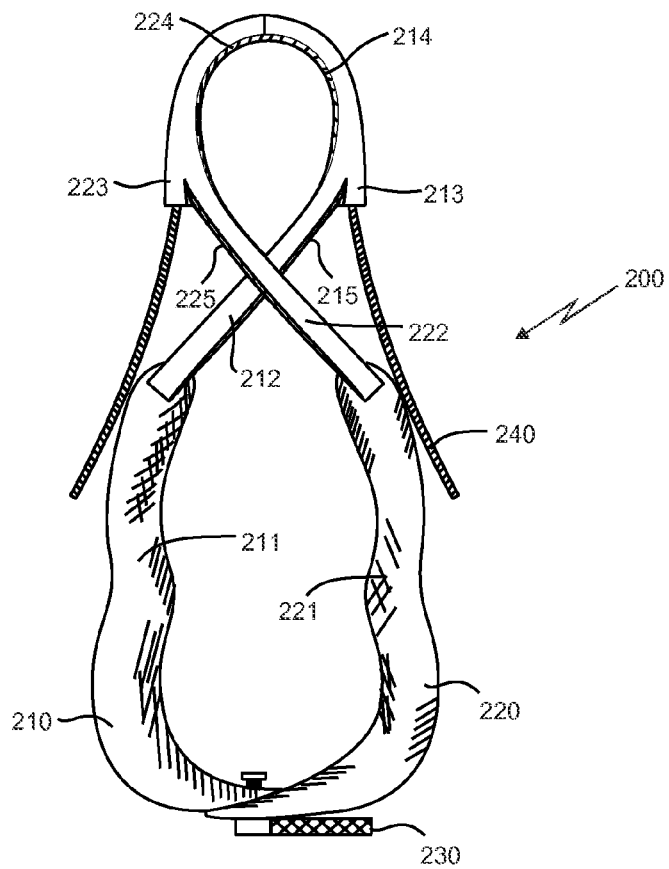
FIG. 18 is a front view of a second additional embodiment of the minimally invasive device for surgical procedures subject of the present invention.

With reference to FIG. 18, it shows a second additional embodiment of minimally invasive device for surgical procedures 200 subject of the present invention, which is formed by at least a pair of assembly elements formed by a primary main body 210 and a secondary main body 220 which cross each other at their intermediate section, and which are assembled at their proximal and distal ends, where primary main body 210 is formed by primary holding handle 211 and primary positioning element 212, and secondary main body 220 is formed by secondary holding handle 221 and secondary positioning element 222; a fastening element 230 which is inserted in the distal end of both primary and secondary main bodies 210 and 220 respectively, a threading element (such as the threading element 28 shown in FIGS. 1 and 5) which is located on the inside of primary positioning element 212 and secondary positioning element 222, and a multifunction element 240 which is located on the inside of the threading element.

In a front view, primary main body 210 is shaped as a 180° inverted letter "S", being formed by primary holding handle 211 of preferably circular section, which forms the lower part of the primary main body in the shape of an inverted letter "S", projecting from the base of its distal end to approximately the middle section of said primary main body 210, and a primary positioning element 212 which projects from the end of primary holding handle 211 to the proximal end of primary main body 210, forming the central and upper parts of the primary main body in the shape of an inverted letter "S".

The body of primary positioning element 212 is of cylindrical shape, with a hollow interior and a hollow primary tangential appendix 213 located on its outer face, at the starting point of the upper curvature of the "S". Said primary positioning element 212 has a first internal slit 214 which runs longitudinally along its inner face from the proximal end to approximately two third parts of the total length of said primary positioning element 212. In addition, said primary positioning element has a first external slit 215 which runs longitudinally along its outer face from where primary tangential appendix 213 is located to where said primary positioning element 212 ends.

Secondary main body 220 is a mirror image of primary main body 210, that is to say, said secondary main body 220 has the shape of a letter "S", and is formed by a secondary holding handle 221 of preferably circular section, which forms the lower part of the main body in the shape of a letter "S", projecting from the base of its distal end to approximately the intermediate section of said secondary main body 220, and a secondary positioning element 222 which projects from where the secondary holding handle 221 ends to the proximal end of secondary main body 220 forming the central and upper parts of the primary main body in the shape of a letter "S".

The body of secondary positioning element 222 is of cylindrical shape, with a hollow interior and has a hollow secondary tangential appendix 223 located on its external face, at the starting point of the upper curvature of the "S". Said secondary positioning element 222 has a second internal slit 224 which runs longitudinally along its internal face from its proximal end to approximately two third parts of the total length of said secondary positioning element 222. In addition, said positioning element 222 has a second external slit 225 which runs longitudinally along its outer face from the second tangential appendix 223 to where said secondary positioning element 222 ends.

Fastening element 230 is inserted in the distal end of primary main body 210 and secondary main body 220 and has the function of joining said bodies together and preventing their unintentional separation. Said fastening element 230 has the same features as fastening element 30 described in the preferred embodiment of the present invention.

Device 200 includes a threading element (such as the threading element 28 shown in FIGS. 1 and 5), which is placed on the inside of primary positioning element 212 of primary main body 210 and of secondary positioning element 222 of secondary main body 220 once both main bodies 210 and 220 are joined together at their proximal and distal ends. The threading element houses multifunction element 240, which has the same features and functions of multifunction element 40 described in the preferred embodiment.

Figure 19:
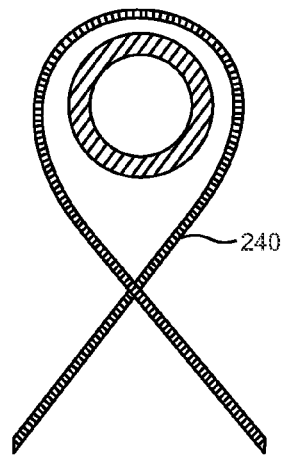
FIG. 19 is a schematic view that portrays a primary trajectory of the multifunction element around a bone structure, according to the configuration of the device for surgical procedures shown in FIG. 18.
Figure 20:
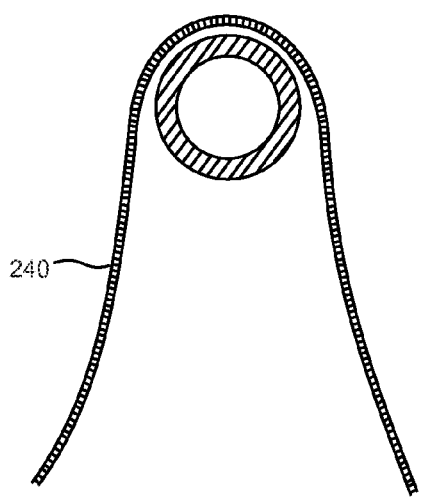
FIG. 20 is a schematic view which portrays a secondary trajectory of the multifunction element around a bone structure, according to the configuration of the device for surgical procedures shown in FIG. 18.

The threading element has two different trajectories, in a first trajectory, said element is placed following the online defined by primary positioning element 212 and secondary positioning element 222, that is to say, the trajectory of said threading element is crossed in a loop, as observed in FIG. 19. In a second trajectory, said threading element is inserted in the primary tangential appendix 213 or in the second tangential appendix 223, continues to the proximal end of device 200 and exits through the opposite tangential appendix with respect to the one through which it entered, this second trajectory resembling the shape of a "U", as shown in FIG. 20. Having two trajectory options in the same device, has the advantage of initiating with a primary trajectory for the threading operation, and later changing the trajectory of multifunction element 240, for example, cross threading of the Gigli saw and subsequently uncrossing it to carry out a "U" cut without the need to remove device 200. This is made possible by slits both in its inner and outer faces.

Figure 21:
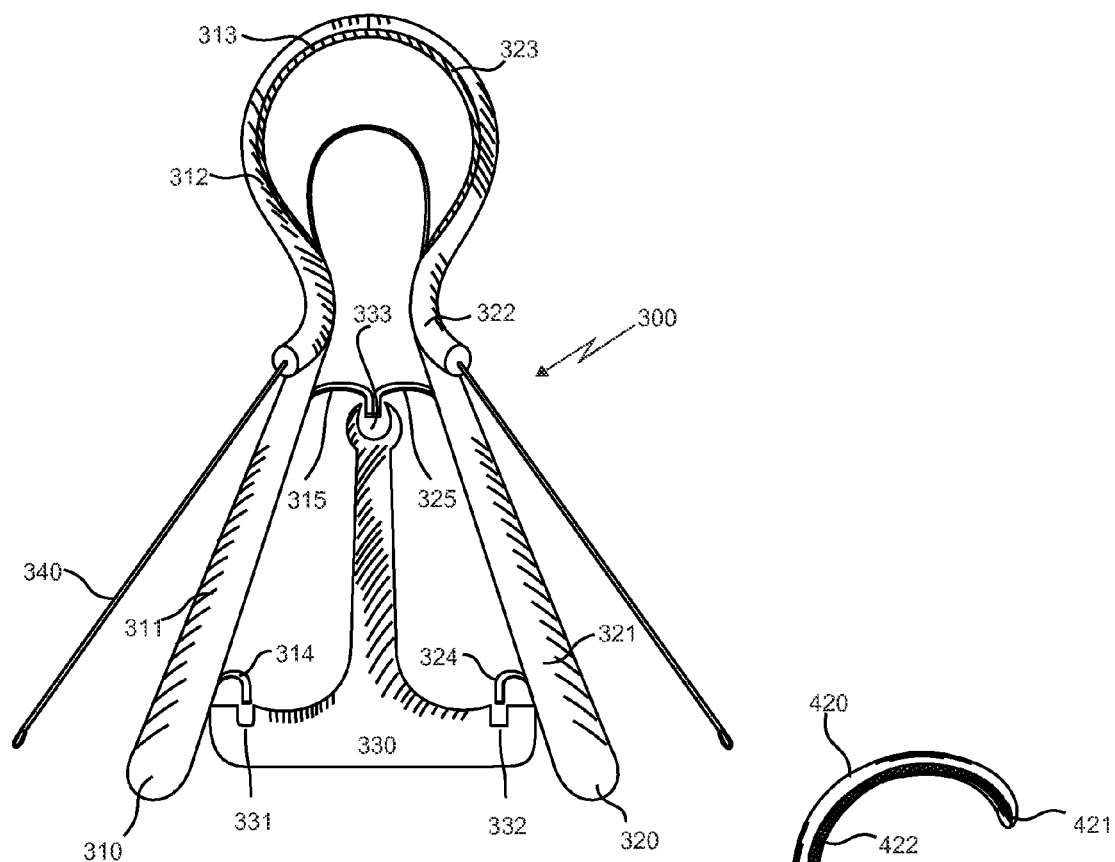
FIG. 21 is a front view of a third additional embodiment of the minimally invasive device for surgical procedures subject of the present invention.

Now, referencing FIG. 21, it shows a third embodiment of the minimally invasive device for surgical procedures 300, which is formed by at least a couple of assembly elements formed by a primary main body 310 and a secondary main body 320 joined at their proximal end, a coupling element 330 which joins both primary and secondary main bodies 310 and 320 joined at their proximal end; a coupling element 330 which joins both primary and secondary main bodies 310 and 320 respectively at their intermediate section and at their distal end, a threading element (such as the threading element 28 shown in FIGS. 1 and 5) which is placed internally starting from the intermediate section of device 300, continues to its proximal end and returns to said intermediate section, and a multifunction element 340 which is located inside the threading element.

Primary main body 310 is formed by a primary holding handle 311 which projects upwards from its distal end to approximately two third parts of the total length of said main body 310; and a primary positioning body 312, which projects from the end of primary holding handle 311 to the proximal end of said primary main body 310. Primary holding handle 311 is a solid body with an ergonomic shape to provide a better grip to the user of the present device 100, while first positioning body 312 is a hollow body of preferably cylindrical shape, which has a curved trajectory which resembles a semi hook. Said primary positioning body 321 has a first slit 313 which runs from its proximal end to approximately two third parts of the total length of said positioning body 312.

Located at the lower end of primary holding handle 311 and particularly on its inner face is first hooking element 314, while a second hooking element 315 is located on the intermediate section on its inner face, the function of which will be described below.

Secondary main body 320 is a mirror image of primary main body 310, that is to say, includes a secondary holding handle 321 and a secondary positioning body 322. Said secondary positioning body 322 has a second slit 323 that runs from its proximal end to approximately two third parts of the total length of said secondary positioning body 322. In addition, at the lower end of secondary holding handle 321, and particularly on its inner face, a third hooking element 324 is located, while a fourth hooking element 325 is located on the inner face of intermediate section, the function of which will be described later.

Coupling element 330 has the shape of a 180° inverted letter "T" in a front view, and has primary and secondary hooking cavities 331 and 332 respectively on each end of its lower horizontal section, which engage with first hooking element 314 of primary holding handle 311 and with third hooking element 324 of secondary holding handle 321 respectively. In addition, said coupling element 330 has a third hooking cavity 333 on the upper end of its vertical section, which engages second hooking element 315 of primary holding handle 311, and fourth hooking element 325 of secondary holding handle 321, thus joining and keeping in position primary main body 310 and secondary main body 320.

Once both main bodies 310 and 320 are joined, an internal channel is created at its proximal end, where the threading element with multifunction element 340 inside it is inserted, said elements having the same features as threading element 28 and multifunction element 40 described in the preferred embodiment of the present invention.

If device 300 is used for cutting bone structures, it is possible to attach a horizontal arm (not shown in the figures) to one of the holding handles 311 or 321 of the present device, at the ends of which external anchoring elements (not shown in the figures) are placed as described in the preferred embodiment of the present invention.

In a fourth additional embodiment of device for surgical procedures 400, it is formed by a single body 401, which has a holding handle 410 which projects upward from its distal end to approximately two third parts of the total length of said body 400, and a cutting body 420, which projects from where holding handle 410 ends to the proximal end of said body 400.

Figure 22:
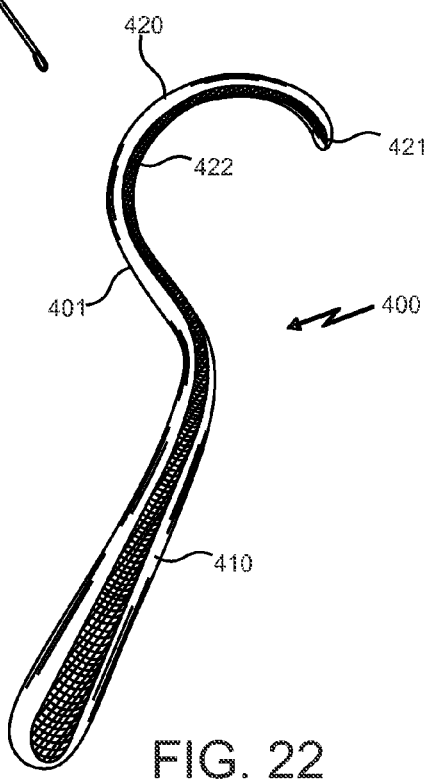
FIG. 22 is a front view of a fourth additional embodiment of the minimally invasive device for surgical procedures subject of the present invention.

Holding handle 410 has an ergonomic shape to provide a better grip to the user of the present device 100. Cutting body 420 is a hollow body of preferably cylindrical shape, which has a curved trajectory which resembles a hook, with a proximal end with a blunt tip 421 in the shape of a decolator, as can be seen in FIG. 22. Said cutting body 420 has an opening 422 along its entire length, which facilitates the cutting of a bone structure.

The fourth additional embodiment of the present device 400 is very useful in surgical procedures which require a broad approach, as for instance osteotomies in the course of an amputation, in hip prosthesis because of arthrosis, in which, after dislocating the hip, it is required to carry out an osteotomy of the femoral neck. Since device 400 consists of a single body 401, assembly delays are avoided, which results in a reduction of the time required for the surgical procedure, thus decreasing bleeding in the patient.

Even though in the above description, preferred embodiments of the present invention have been described and shown, it must be stressed that numerous modifications to the same are possible without deviating from the true scope of the invention, such as modifications to the configuration of holding handles and coupling elements, modifications to the section of the different elements which form part of the present device, modifying the fastening element, etc.

Therefore, the present invention must not be restricted except by what may be required because of the prior art and the attached claims.

The invention claimed is:

1. A minimally invasive device for surgical procedures, the device comprising:
   at least one pair of assembly elements formed by a primary main body and a secondary main body each having a proximal end, a distal end, and an intermediate section, wherein the primary main body and the secondary main body are joined together at their proximal ends and at their distal ends;
   a fastening element which is inserted in the distal ends of both the primary and secondary main bodies, and which is employed to keep the distal ends of both the primary and secondary main bodies joined together;
   a threading element inserted in the intermediate section of one of the primary main body and the secondary main body, continues to the proximal end of at least one of the primary main body and the secondary main body, and returns to the intermediate section of the other one of the primary main body and the secondary main body; and
   a multifunction element located inside the threading element;
   wherein the fastening element comprises a central handle with an outer surface having a plurality of channels which cross each other to form a rough surface which increases friction of said central handle for gripping thereof, and comprises a boss located on a lower end of the central handle and positioned perpendicularly to the central handle, with a threaded cylinder having a smaller diameter than said boss projecting from an inner face of the boss and inserted in an orifice of an anchoring area of the primary main body; where the threaded cylinder is arranged to be securely held by the fastening element.

2. A minimally invasive device for surgical procedures according to claim 1, wherein the central handle has a substantially cylindrical shape, and the boss has a substantially cylindrical outline.

3. A minimally invasive device for surgical procedures according to claim 1, wherein on a side opposite to where the boss is located, the threaded cylinder has a projection of larger diameter than the orifice in the anchoring area; and wherein said projection is an integral part of the threaded cylinder.

4. A minimally invasive device for surgical procedures, the device comprising:
   at least one pair of assembly elements formed by a primary main body and a secondary main body each having a proximal end, a distal end, and an intermediate section, wherein the primary main body and the secondary main body are joined together at their proximal ends and at their distal ends;
   a fastening element which is inserted in the distal ends of both the primary and secondary main bodies, and which is employed to keep the distal ends of both the primary and secondary main bodies joined together;
   a threading element inserted in the intermediate section of one of the primary main body and the secondary main body, continues to the proximal end of at least one of the primary main body and the secondary main body, and returns to the intermediate section of the other one of the primary main body and the secondary main body; and
   a multifunction element located inside the threading element;
   wherein the device further includes a spatial positioning element which allows the device to direct, measure, and graduate the cut of a bone structure on frontal, sagittal, and rotational spatial planes, wherein the spatial positioning element is configured to be firmly attached to the bone structure to be cut, by at least a pair of bone structure fastening elements external to the minimally invasive device for surgical procedures, employing an anchoring mechanism.

5. A minimally invasive device for surgical procedures according to claim 4, wherein the spatial positioning element comprises a straight arm and a curved arm, the straight arm having a flat rectangular elongated body including a first central longitudinal channel which traverses the entire thickness of the body and runs along the entire length of the body, and over which the anchoring mechanism slides and locks, wherein said straight arm has a first indicating scale positioned on an upper face of the straight arm, which indicates displacement of the device on a front plane (varus-valgus) to a user of the device.

6. A minimally invasive device for surgical procedures according to claim 5, wherein the straight arm has two terminal ends and a primary anchoring point located at one of the terminal ends, wherein the primary anchoring point has a central orifice where an external anchoring element is inserted, and wherein at the other one of the terminal ends a sliding point is located, and over which the curved arm slides and locks.

7. A minimally invasive device for surgical procedures according to claim 6, wherein the primary anchoring point comprises a substantially quadrangular shape, and the sliding point is substantially C-shaped.

8. A minimally invasive device for surgical procedures according to claim 6, wherein the curved arm comprises a curved body having a curvature with a radius having the same center as a center of the bone structure to be cut and having a second central longitudinal channel traversing an entire thickness of the curved body and being employed to lock said curved arm to the sliding point with a screw which is threadingly inserted in an orifice located in the sliding point, and wherein said curved arm has a second indicating scale positioned on a front face of the curved arm to allow measurement of an angle of rotation of the device with respect to the bone structure.

9. A minimally invasive device for surgical procedures according to claim 5, wherein the primary main body comprises a primary holding handle, the secondary main body comprises a secondary holding handle, and one of the primary holding handle or the secondary holding handle includes a projection which projects longitudinally and in an ascending direction following a straight trajectory, from approximately half of the primary holding handle or secondary holding handle to a distance coinciding with an end of the primary holding handle or the secondary holding handle.

10. A minimally invasive device for surgical procedures according to claim 9, wherein the projection comprises a substantially cylindrical shape.

11. A minimally invasive device for surgical procedures according to claim 5, wherein the anchoring mechanism comprises a central body including a front face having an orifice in which an appendix of the primary holding handle or an appendix of the secondary holding handle is inserted and secured; and the device includes a rotation element located on an upper face of said central body and that can rotate with respect to the central body, wherein the rotation element has an indentation including a central part having a threaded orifice over which the straight arm is positioned and secured by a bolt inserted in the first central longitudinal channel and in said threaded orifice.

12. A minimally invasive device for surgical procedures according to claim 11, wherein the central body comprises a substantially cylindrical shape.

13. A minimally invasive device for surgical procedures according to claim 5, wherein the spatial positioning element further includes an intermediate arm placed under the straight arm and having a flat elongated body of substantially rectangular shape and including a third central channel which traverses the entire flat elongated body and runs along an entire length of the flat elongated body.

14. A minimally invasive device for surgical procedures according to claim 4, wherein the fastening elements are selected from a group consisting of Kirschner pins and Steinmann pins.

15. A minimally invasive device for surgical procedures according to claim 4, wherein the fastening elements comprise Kirschner pins.

16. A minimally invasive device for surgical procedures, the device comprising:
at least one pair of assembly elements formed by a primary main body and a secondary main body each having a proximal end, a distal end, and an intermediate section, wherein the primary main body and the secondary main body are joined at their proximal ends;
a coupling element which joins both primary and secondary main bodies at their intermediate sections and at their distal ends;
a threading element which is placed internally from the intermediate section of at least one of the primary main body and the second main body, continues to the proximal end of at least one of the primary main body and the second main body, and returns to the intermediate section of the at least one of the primary main body and the second main body; and
a multifunction element located on the inside of the threading element.

17. A minimally invasive device for surgical procedures according to claim 16, wherein the primary main body includes of a primary holding handle which projects upwards from the distal end of the main body to approximately two-thirds a total length of said primary main body, and includes a primary positioning body projecting from an end of the primary holding handle to the proximal end of said primary main body, wherein said primary holding handle is of ergonomic shape to facilitate gripping by a user of the device, wherein the primary positioning body has a curved trajectory which resembles a semi hook; and has a first slit running from a proximal end of the primary positioning body to approximately two-thirds of a total length of said primary positioning body.

18. A minimally invasive device for surgical procedures according to claim 17, wherein a first hooking element is located at a lower end of the primary holding handle on an inner face of the primary holding handle, and a second hooking element is located at a height of an intermediate section of the primary holding handle.

19. A minimally invasive device for surgical procedures according to claim 16, wherein the secondary main body has a secondary holding handle and a secondary positioning body; wherein said secondary positioning body has a second slit which runs from a proximal end of the secondary positioning body to approximately two-thirds of a total length of said secondary positioning body, wherein a third hooking element is located at a lower end of the secondary holding handle on an inner face of the secondary holding handle, and wherein a fourth coupling element is located at a height of an intermediate section on the inner face of the secondary holding handle.

20. A minimally invasive device for surgical procedures according to claim 16, wherein once the primary and secondary main bodies are joined at their proximal end, an internal channel is formed in which is inserted the threading element with the multifunction element inside the threading element.

* * * * *